(12) United States Patent
Harrison et al.

(10) Patent No.: US 7,473,684 B2
(45) Date of Patent: Jan. 6, 2009

(54) BISPHOSPHONATE FORMULATION

(75) Inventors: Paul Jonathan Harrison, Dublin (IE); Anna Marie Power, Dublin (IE)

(73) Assignee: Selamine Limited, Dublin (IE)

( * ) Notice: Subject to any disclaimer, the term of this patent is extended or adjusted under 35 U.S.C. 154(b) by 0 days.

(21) Appl. No.: 11/439,427

(22) Filed: May 24, 2006

(65) Prior Publication Data

US 2007/0065507 A1 Mar. 22, 2007

Related U.S. Application Data

(60) Provisional application No. 60/813,586, filed on Feb. 21, 2006.

(30) Foreign Application Priority Data

Sep. 16, 2005 (GB) .................................. 0518952

(51) Int. Cl.
*A61K 31/66* (2006.01)
*A61K 31/685* (2006.01)

(52) U.S. Cl. ........................................ 514/78; 514/102

(58) Field of Classification Search ........................ None
See application file for complete search history.

(56) References Cited

U.S. PATENT DOCUMENTS

| | | | |
|---|---|---|---|
| 4,432,968 A * | 2/1984 | Page et al. .................. 424/497 |
| 5,073,384 A | 12/1991 | Valentine et al. |
| 5,096,717 A | 3/1992 | Wirth et al. |
| 5,853,759 A * | 12/1998 | Katdare et al. .............. 424/466 |
| 5,914,135 A | 6/1999 | Dubek et al. |
| 6,015,801 A | 1/2000 | Daifotis et al. |
| 6,080,431 A | 6/2000 | Andon et al. |
| 6,248,363 B1 | 6/2001 | Patel et al. |
| 6,372,728 B1 * | 4/2002 | Ungell ........................ 514/109 |
| 6,458,383 B2 * | 10/2002 | Chen et al. .................. 424/451 |
| 6,569,463 B2 | 5/2003 | Patel et al. |
| 6,702,803 B2 * | 3/2004 | Kupperblatt et al. ..... 604/890.1 |
| 6,753,009 B2 * | 6/2004 | Luber et al. ................. 424/441 |
| 6,835,722 B1 | 12/2004 | Kang et al. |
| 6,923,988 B2 | 8/2005 | Patel et al. |
| 2002/0022603 A1 * | 2/2002 | Lichtenberger ............... 514/78 |
| 2003/0055067 A1 * | 3/2003 | Sharpe et al. .......... 514/254.05 |
| 2003/0158154 A1 | 8/2003 | Fleshner-Barak |
| 2003/0176397 A1 * | 9/2003 | Lichtenberger ............... 514/78 |
| 2003/0180352 A1 | 9/2003 | Patel et al. |
| 2003/0206877 A1 | 11/2003 | Lenzi-Brangi et al. |
| 2004/0023931 A1 | 2/2004 | Roldan et al. |
| 2004/0062802 A1 | 4/2004 | Hermelin |
| 2004/0063670 A1 * | 4/2004 | Fox et al. ..................... 514/102 |
| 2004/0142905 A1 * | 7/2004 | Wang ......................... 514/78 |
| 2005/0013862 A1 | 1/2005 | Tobyn et al. |
| 2005/0056809 A1 | 3/2005 | Silverman et al. |
| 2005/0070504 A1 | 3/2005 | Burgio, Jr. et al. |
| 2005/0101576 A1 | 5/2005 | Whitehouse et al. |
| 2005/0125054 A1 | 6/2005 | Bhat et al. |
| 2005/0181050 A1 | 8/2005 | Hirsh et al. |
| 2005/0186267 A1 | 8/2005 | Thompson et al. |
| 2005/0192246 A1 * | 9/2005 | Hostetler et al. ............... 514/47 |
| 2005/0260262 A1 * | 11/2005 | Dansereau et al. .......... 424/464 |
| 2006/0120997 A1 | 6/2006 | Lipton |
| 2008/0032011 A1 * | 2/2008 | Liniger et al. ............... 426/250 |

FOREIGN PATENT DOCUMENTS

| WO | WO 93/09785 A1 | 5/1993 |
| WO | WO 98/14196 A1 | 4/1998 |
| WO | WO 2004/024166 A1 | 3/2004 |
| WO | WO 2005/115331 A2 | 12/2005 |

OTHER PUBLICATIONS

English language abstract of JP 02229115 A, 1 page.
English language abstract of JP 05238929 A, 2 pages.
Smart, H.L., "Comparison of a dimethicone/antacid (Asilone gel) with an alginate/antacid (Gaviscon liquid) in the management of reflux oesophagitis," *J. Royal Society of Med.* 83:554-556, The Royal Society of Medicine (1990).

* cited by examiner

*Primary Examiner*—S. Tran
(74) *Attorney, Agent, or Firm*—Sterne, Kessler, Goldstein & Fox P.L.L.C.

(57) ABSTRACT

A bisphosphonate for treatment of osteoporosis is formulated with an amount of an antifoaming agent effective for reducing foaming in the stomach, leading to reduced reflux and oesophageal irritation in use and increased patient compliance.

39 Claims, No Drawings

BISPHOSPHONATE FORMULATION

FIELD OF THE INVENTION

The present invention relates to formulations comprising bisphosphonates and their use in treatment of various conditions, especially such formulations for treatment of osteoporosis.

BACKGROUND TO THE INVENTION

Osteoporosis is a disease of bone in which the amount of bone is decreased and the strength of trabecular bone is reduced, cortical bone becomes thin and bones are susceptible to fracture.

It is estimated that 10 million Americans have established osteoporosis and another 34 million have osteopenia, or low bone mass, which leads to osteoporosis. The disease is responsible for 1.5 millions fractures annually, mostly involving the lumbar vertebrae, hip, and wrist.

Patients who are at risk for osteoporosis can be treated with vitamin D and calcium supplements. Bisphosphonates are also commonly used in the prophylaxis and treatment of osteoporosis and corticosteroid-induced osteoporosis. Bisphosphonates are synthetic analogues of natural pyrophosphate that inhibit osteoclast activity and decrease bone turnover and resorption.

The bisphosphonates alendronic acid and risedronate sodium are considered the drugs of choice for treatment of osteoporosis, but disodium etidronate may also be used. Treatment results in lower fracture rates and higher bone density in both male and female patients. Lifestyle changes are also generally prescribed for sufferers.

Whilst it is known to treat osteoporosis with bisphosphonates, there are a number of gastrointestinal symptoms associated with this class of drugs such as abdominal pain, dyspepsia, diarrhoea or constipation. Severe gastrointestinal reactions and oesophageal reactions such as oesophagitis, erosions, and ulceration have occurred. As a consequence biphosphonates should not be administered to patients with abnormalities of the oesophagus or other factors that might delay oesophageal emptying, or those unable to stand, or sit upright for at least 30 minutes (Martindale). Strict instructions are set out for taking these drugs, patients taking alendronate are instructed to take it on an empty stomach before food and to remain sitting upright without eating for at least 30 minutes after taking the drug. Similar instructions, in some case stricter, apply for other bisphosphonates.

The reason for these instructions is that alendronate and other bisphosphonates can provoke severe oesophageal irritation. This can lead to reflux into the oesophagus and consequent ulceration, oesophagitis, heartburn and retrosternal pain, pain on swallowing and dysphagia. In addition to these side-effects, there is reduced patient compliance with the bisphosphonate treatment, leading to progression of the osteoporosis.

Bisphosphonate treatment is so effective that it is very widely used. Patients have hitherto had to put up with the adverse symptoms associated with bisphosphonate use as there is no alternative treatment that gives such good results.

WO 93/09785 and US 2003/0158154 disclose bisphosphonate formulations that contain very small amounts of surfactant, including in some instances simethicone, to facilitate tablet manufacture and give tablets a glossy appearance.

An object of the invention is to ameliorate the above problems and disadvantages. An object of a specific embodiment of the invention is to provide a formulation of a bisphosphonate which provokes reduced gastric irritation and/or reduced reflux of stomach acid, leading preferably to increased patient compliance.

SUMMARY OF THE INVENTION

Accordingly the present invention provides a pharmaceutical formulation comprising a bisphosphonate and an antifoaming agent, and also provides for administration of a bisphosphonate in combination with an antifoaming agent.

In use, for example in treatment of osteoporosis, enough antifoaming agent is present for the combination to be expected to limit the formation of foams in the stomach. Without wishing to be bound by any particular theory, it is believed that the associated concomitant decrease in the volume of stomach contents, and additionally barrier properties of some preferred antifoaming agents, will reduce the likelihood of stomach acid reflux and therefore oesophageal irritation. Hence, typical formulations of the invention comprise an amount of an antifoaming agent effective to reduce the formation of foam in the stomach.

The antifoaming agent may comprise an agent to lower surface tension and/or to reduce the foaming tendency of stomach contents, and more than one agent may be advantageously used in concert to reduce foaming, and, in preferred embodiments also provide barrier protection.

Formulations of the present invention may comprise an amount of an antifoaming agent in the range of 20 mg to 150 mg, preferably from 35 mg to 125 mg and specific embodiments set out in examples below have antifoaming agent present in the range of 50 mg to 100 mg—according to the United States Pharmacopeia, the minimum quantity of simethicone effective for reducing foam formation in the stomach is 20 mg. The invention also provides formulations that comprise at least 1%, preferably at least 2% antifoaming agent, and more generally an amount of an antifoaming agent in the range of 3% to 40% by weight, and preferably in the range of 5% to 30% by weight. Specific embodiments set out in the examples contain from about 7% to about 18% antifoaming agent by weight.

Antifoaming agents are known to those of skill in the art. Whilst many different agents may be used in the formulations of the invention, presently there are only a limited number of approved antifoaming agents available for pharmaceutical formulations, and these are particularly suitable. Siloxanes can be used. Some embodiments use one or more polydimethylsiloxanes as the antifoaming agent. Preferred embodiments of the formulation of the invention comprise dimethicone BP, simethicone BP (an activated form of dimethicone), or both.

Any bisphosphonate having the side-effect of promoting gastric irritation may suitably be used in the formulations of the invention. The invention applies generally to formulations of bisphosphonates, including for example alendronic acid, disodium etidronate, disodium pamidronate, ibandronic acid, risedronate sodium, sodium clodronate, strontium ranelate, tiludronic acid and zoledronic acid. In preferred embodiments the bisphosphonate may be selected from the group consisting of alendronic acid or alendronate, risedronate and etidronate. Particularly preferred formulations comprise alendronic acid or alendronate. Typically the amount of bisphosphonate is from 5 mg to 150 mg of Alendronic acid (or a therapeutically equivalent amount of another bisphosphonate, or an equivalent amount of a bisphosphonate compound), preferably from about 10 mg to about 70 mg. Formulations of the invention comprise also a pharmaceutically acceptable carrier.

Bisphosphonates can be co-administered with other agents helpful in treatment of osteoporosis, either directly or dealing e.g. with side effects of the treatment. Formulations of the invention may thus also include one or more of a vitamin D derivative and a calcium supplement.

The term 'Vitamin D derivative' is used for a range of compounds which have the ability to prevent or treat rickets. Vitamin D supplements suitable for inclusion in formulations of the invention include ergocalciferol (calciferol, vitamin D2), cholecalciferol (vitamin D3), dihydrotachysterol, alfa-calcidol (1α-hydroxycholecalciferol), and calcitriol (1,25-dihydroxycholecalciferol).

Some calcium supplements which may be used in the formulations of the invention are calcium salts, optionally selected from calcium gluconate, calcium chloride, calcium lactate, ADCAL®, CACIT®, CALCICHEW®, CALCIUM-500®, CALCIUM-SANDOZ®and SANDOCAL®. Treatments of the invention may also be carried out in combination with parenteral calcium supplements.

Particularly preferred formulations of the invention comprise a bisphosphonate, antifoaming agent, a vitamin D derivative and a calcium supplement.

Formulations of the invention include an amount of one or more agents effective for reducing the tendency of the stomach contents to foam, and which may also elicit barrier protection. Treatment according to the invention involves the administration of one or more such agents with bisphosphonates simultaneously, either together (in the same formulation) or separately (taken together at the same time), or separately (time delayed administration).

Hence, the bisphosphonate and the antifoaming agent can be taken separately. In these embodiments the antifoaming agent is generally taken up to 1 hour before and not more than 10 minutes after the bisphosphonate. Preferably the antifoaming agent is taken not more than 10 minutes before and more preferably not more than 5 minutes before the bisphosphonate.

In a further aspect the invention provides a kit including a bisphosphonate and an amount of an antifoaming agent effective for reducing the formation of foam in the stomach. Preferred kits include other actives such as vitamin D derivatives and/or calcium supplements.

In another aspect the invention provides for the use of an antifoaming agent in the manufacture of a medicament effective for the treatment or prophylaxis of osteoporosis in combination with a bisphosphonate. The invention also provides for the use of a bisphosphonate in the manufacture of a medicament for the treatment or prophylaxis of osteoporosis in combination with an antifoaming agent. Preferably the bisphosphonate is alendronate and the antifoaming agent is a siloxane. The medicament may advantageously contain other actives as outlined herein.

For the purposes of the present specification the phrase 'treatment or prophylaxis of osteoporosis' means any and all treatment or prophylaxis for Paget's disease, osteopenia, osteoporosis and corticosteroid-induced osteoporosis.

The invention also provides methods for the treatment of osteoporosis comprising administration to a patient of a bisphosphonate and an antifoaming agent.

The formulations, methods, kits and uses discussed offer potential reduced mucosal irritation, gastric irritation and/or oesophageal irritation when compared to the art known bisphosphonate formulations. An anticipated advantage of the invention is hence that this irritation is reduced. Further anticipated advantages are that instructions to patients, which hitherto gave strict advice as to how to take the medicament, can be relaxed and lower irritation will naturally lead to greater patient compliance with the medication regime and greater overall effectiveness of treatment.

EXAMPLES

Various aspects of the invention will now be described with reference to the accompanying Examples. The examples are not to be construed as limiting the scope of the invention as claimed herein. One of skill in the pharmaceutical arts will understand that some of the ingredients of the formulations given in the examples may be substituted with known equivalent ingredients. These formulations comprise a bisphosphonate for treatment of osteoporosis in combination with an amount of an antifoaming agent effective for reducing foam formation in the stomach, and are within the scope of the invention.

Example 1

| | |
|---|---|
| Alendronic acid 70 mg (as sodium alendronate trihydrate) | 91.4 mg |
| Dimeticone B.P. | 50.0 mg |
| Microcrystalline cellulose B.P. | 140.0 mg |
| Lactose B.P. | 110.0 mg |
| Croscarmellose sodium B.P. | 6.0 mg |
| Dehydrated Alcohol USP | q.s. |
| Colloidal anhydrous silica B.P. | 1.0 mg |
| Magnesium stearate | 2.0 mg |
| Total | 400.4 mg |

Example 2

| | |
|---|---|
| Alendronic acid 70 mg (as sodium alendronate trihydrate) | 91.4 mg |
| Simeticone B.P. | 50.0 mg |
| Microcrystalline cellulose B.P. | 140.0 mg |
| Calcium carbonate B.P. | 105.0 mg |
| Povidone B.P | 6.0 mg |
| Croscarmellose sodium B.P. | 5.0 mg. |
| Dehydrated Alcohol USP | q.s |
| Colloidal anhydrous silica B.P. | 1.0 mg |
| Magnesium stearate | 2.0 mg |
| Total | 400.4 mg |

Example 3

| | |
|---|---|
| Alendronic acid 70 mg (as sodium alendronate trihydrate) | 91.4 mg |
| Simeticone B.P. | 25.0 mg |
| Dimethicone B.P. | 25.0 mg |
| Microcrystalline cellulose B.P. | 140.0 mg |
| Magnesium carbonate B.P. | 110.0 mg |
| Croscarmellose sodium B.P. | 6.0 mg |
| Dehydrated Alcohol USP | q.s. |
| Colloidal anhydrous silica B.P. | 1.0 mg |
| Magnesium stearate | 2.0 mg |
| Total | 400.4 mg |

Example 4

| | |
|---|---|
| Alendronic acid 70 mg (as sodium alendronate trihydrate) | 91.4 mg |
| Dimeticone B.P. | 50.0 mg |
| Microcrystalline cellulose B.P. | 140.0 mg |
| Sucrose B.P. | 110.0 mg |
| Croscarmellose sodium B.P. | 6.0 mg |
| Dehydrated Alcohol USP | q.s. |
| Colloidal anhydrous silica B.P. | 1.0 mg |
| Magnesium stearate | 2.0 mg |
| Total | 400.4 mg |

Example 5

| | |
|---|---|
| Alendronic acid 70 mg (as sodium alendronate trihydrate) | 91.4 mg |
| Dimeticone B.P. | 50.0 mg |
| Microcrystalline cellulose B.P. | 140.0 mg |
| Lactose B.P. | 110.0 mg |
| Croscarmellose sodium B.P. | 6.0 mg |
| Isopropyl Alcohol USP | q.s. |
| Colloidal anhydrous silica B.P. | 1.0 mg |
| Magnesium stearate | 2.0 mg |
| Total | 400.4 mg |

Example 6

| | |
|---|---|
| Alendronic acid 70 mg (as sodium alendronate trihydrate) | 91.4 mg |
| Dimeticone B.P. | 50.0 mg |
| Microcrystalline cellulose B.P. | 140.0 mg |
| Lactose B.P. | 110.0 mg |
| Croscarmellose sodium B.P. | 6.0 mg |
| Purified Water | q.s. |
| Colloidal anhydrous silica B.P. | 1.0 mg |
| Magnesium stearate | 2.0 mg |
| Total | 400.4 mg |

Example 7

| | |
|---|---|
| Alendronic acid 70 mg (as sodium alendronate trihydrate) | 91.4 mg |
| Dimeticone B.P. | 50.0 mg |
| Microcrystalline cellulose B.P. | 140.0 mg |
| Lactose B.P. | 110.0 mg |
| Croscarmellose sodium B.P. | 6.0 mg |
| Dehydrated Alcohol USP | q.s. |
| Colloidal anhydrous silica B.P. | 1.0 mg |
| Stearic Acid | 2.0 mg |
| Total | 400.4 mg |

Example 8

| | |
|---|---|
| Alendronic acid 70 mg (as sodium alendronate trihydrate) | 91.4 mg |
| Dimeticone B.P. | 100.0 mg |
| Microcrystalline cellulose B.P. | 280.0 mg |
| Lactose B.P. | 113.0 mg |
| Croscarmellose sodium B.P. | 12.0 mg |
| Dehydrated Alcohol USP | q.s. |
| Colloidal anhydrous silica BP | 2.0 mg |
| Magnesium stearate | 3.0 mg |
| Total | 601.4 mg |

Example 9

| | |
|---|---|
| Alendronic acid 70 mg (as sodium alendronate trihydrate) | 91.4 mg |
| Simeticone B.P. | 100.0 mg |
| Microcrystalline cellulose B.P. | 280.0 mg |
| Lactose B.P. | 113.0 mg |
| Croscarmellose sodium B.P. | 12.0 mg |
| Dehydrated Alcohol USP | q.s. |
| Colloidal anhydrous silica BP | 2.0 mg |
| Magnesium stearate | 3.0 mg |
| Total | 601.4 mg |

Example 10

| | |
|---|---|
| Alendronic acid 70 mg (as sodium alendronate trihydrate) | 91.4 mg |
| Dimeticone B.P. | 50.0 mg |
| Simeticone B.P. | 50.0 mg |
| Microcrystalline cellulose B.P. | 280.0 mg |
| Lactose B.P. | 113.0 mg |
| Croscarmellose sodium B.P. | 12.0 mg |
| Dehydrated Alcohol USP | q.s. |
| Colloidal anhydrous silica BP | 2.0 mg |
| Magnesium stearate | 3.0 mg |
| Total | 601.4 mg |

Example 11

| | |
|---|---|
| Alendronic acid 70 mg (as sodium alendronate trihydrate) | 91.4 mg |
| Dimeticone B.P. | 100.0 mg |
| Microcrystalline cellulose B.P. | 280.0 mg |
| Sucrose B.P. | 113.0 mg |
| Croscarmellose sodium B.P. | 12.0 mg |
| Dehydrated Alcohol USP | q.s. |
| Colloidal anhydrous silica BP | 2.0 mg |
| Magnesium stearate | 3.0 mg |
| Total | 601.4 mg |

Example 12

| | |
|---|---|
| Alendronic acid 70 mg (as sodium alendronate trihydrate) | 91.4 mg |
| Dimeticone B.P. | 100.0 mg |
| Microcrystalline cellulose B.P. | 280.0 mg |
| Lactose B.P. | 113.0 mg |
| Croscarmellose sodium B.P. | 12.0 mg |
| Isopropyl alchol B.P. | q.s. |
| Colloidal anhydrous silica BP | 2.0 mg |
| Magnesium stearate | 3.0 mg |
| Total | 601.4 mg |

Example 13

| | |
|---|---|
| Alendronic acid 70 mg (as sodium alendronate trihydrate) | 91.4 mg |
| Dimeticone B.P. | 100.0 mg |
| Microcrystalline cellulose B.P. | 280.0 mg |
| Lactose B.P. | 113.0 mg |
| Croscarmellose sodium B.P. | 12.0 mg |
| Purified water B.P. | q.s. |
| Colloidal anhydrous silica BP | 2.0 mg |
| Magnesium stearate | 3.0 mg |
| Total | 601.4 mg |

Example 14

| | |
|---|---|
| Alendronic acid 70 mg (as sodium alendronate trihydrate) | 91.4 mg |
| Dimeticone B.P. | 100.0 mg |
| Microcrystalline cellulose B.P. | 280.0 mg |
| Lactose B.P. | 113.0 mg |
| Croscarmellose sodium B.P. | 12.0 mg |
| Dehydrated Alcohol USP | q.s. |
| Colloidal anhydrous silica BP | 2.0 mg |
| Stearic acid | 3.0 mg |
| Total | 601.4 mg |

Example 15

| | |
|---|---|
| Alendronic acid 10 mg (as sodium alendronate trihydrate) | 13.1 mg |
| Dimeticone B.P. | 50.0 mg |
| Microcrystalline cellulose B.P. | 140.0 mg |
| Lactose B.P. | 80.0 mg |
| Croscarmellose sodium B.P. | 6.0 mg |
| Dehydrated Alcohol USP | q.s |
| Colloidal anhydrous silica BP | 1.0 mg |
| Magnesium stearate | 2.0 mg |
| Total | 292.1 mg |

Example 16

| | |
|---|---|
| Alendronic acid 10 mg (as sodium alendronate trihydrate) | 13.1 mg |
| Simeticone B.P. | 50.0 mg |
| Microcrystalline cellulose B.P. | 140.0 mg |
| Lactose B.P. | 80.0 mg |
| Croscarmellose sodium B.P. | 6.0 mg |
| Dehydrated Alcohol USP | q.s |
| Colloidal anhydrous silica BP | 1.0 mg |
| Magnesium stearate | 2.0 mg |
| Total | 292.1 mg |

Example 17

| | |
|---|---|
| Alendronic acid 10 mg (as sodium alendronate trihydrate) | 13.1 mg |
| Simeticone B.P. | 25.0 mg |
| Dimeticone B.P. | 25.0 mg |
| Microcrystalline cellulose B.P. | 140.0 mg |
| Lactose B.P. | 80.0 mg |
| Croscarmellose sodium B.P. | 6.0 mg |
| Dehydrated Alcohol USP | q.s |
| Colloidal anhydrous silica BP | 1.0 mg |
| Magnesium stearate | 2.0 mg |
| Total | 292.1 mg |

Example 18

| | |
|---|---|
| Alendronic acid 10 mg (as sodium alendronate trihydrate) | 13.1 mg |
| Dimeticone B.P. | 50.0 mg |
| Microcrystalline cellulose B.P. | 140.0 mg |
| Sucrose B.P. | 80.0 mg |
| Croscarmellose sodium B.P. | 6.0 mg |
| Dehydrated Alcohol USP | q.s |
| Colloidal anhydrous silica BP | 1.0 mg |
| Magnesium stearate | 2.0 mg |
| Total | 292.1 mg |

Example 19

| | |
|---|---|
| Alendronic acid 10 mg (as sodium alendronate trihydrate) | 13.1 mg |
| Dimeticone B.P. | 50.0 mg |
| Microcrystalline cellulose B.P. | 140.0 mg |
| Lactose B.P. | 80.0 mg |
| Croscarmellose sodium B.P. | 6.0 mg |
| Isopropyl Alcohol USP | q.s |
| Colloidal anhydrous silica BP | 1.0 mg |
| Magnesium stearate | 2.0 mg |
| Total | 292.1 mg |

Example 20

| | |
|---|---|
| Alendronic acid 10 mg (as sodium alendronate trihydrate) | 13.1 mg |
| Dimeticone B.P. | 50.0 mg |
| Microcrystalline cellulose B.P. | 140.0 mg |
| Lactose B.P. | 80.0 mg |
| Croscarmellose sodium B.P. | 6.0 mg |
| Purified water | q.s |
| Colloidal anhydrous silica BP | 1.0 mg |
| Magnesium stearate | 2.0 mg |
| Total | 292.1 mg |

Example 21

| | |
|---|---|
| Alendronic acid 10 mg (as sodium alendronate trihydrate) | 13.1 mg |
| Dimeticone B.P. | 50.0 mg |
| Microcrystalline cellulose B.P. | 140.0 mg |
| Lactose B.P. | 80.0 mg |
| Croscarmellose sodium B.P. | 6.0 mg |
| Dehydrated Alcohol USP | q.s |
| Colloidal anhydrous silica BP | 1.0 mg |
| Stearic Acid | 2.0 mg |
| Total | 292.1 mg |

The formulations of Examples 1-21 are manufactured according to the following manufacturing examples:

Example 22

To manufacture tablet formulations of the above examples the dry ingredients 1-5 (dry ingredients 1-6 in examples 3, 10 and 17 where both simeticone and dimeticone are included) are mixed together. Item 6 (item 7 for examples 3, 10 and 17) is then added to form a wet granulate suitable for compression. The wet granulate is then dried and milled to give a uniform granule. The dry milled granules are then mixed with excipients 7 & 8 and compressed to a suitable hardness.

Example 23

Tablets are prepared as above (example 22) but item 2 is omitted from the dry mix and then added to the solvent, ie item 6 (or 7), prior to it being added to the dry mix of ingredient. The remaining steps are the same as for example 22.

Example 24

Tablets are prepared as above for example 22 but item 6 (or 7), the solvent of granulation, is omitted and the product is manufactured by direct compression.

Example 25

Ingredients 1-5 (or 1-6) are dry mixed followed by dry milling. The remaining excipients are then blended into the dry ingredients and the resultant mass is compressed to a suitable hardness to give tablets or encapsulated into a suitably sized capsule.

Example 26

A tablet is made in which simeticone granules are manufactured separately and then blended with the other ingredients.

| | | |
|---|---|---|
| 1. | Simeticone B.P. | 100.0 mg |
| 2. | Mannitol B.P. | 400.0 mg |
| 3. | Povidone B.P. | 6.0 mg |
| 4. | Sodium starch glycollate B.P. | 12.0 mg |
| 5. | Purified Water B.P | q.s |
| | sub total | 518.0 mg |

To make the simeticone granules items 1-4 are dry mixed, water is added and then the mixture is wet mixed. The mixture is then dried and milled to give a uniform granule.

| | | |
|---|---|---|
| A. | Alendronic acid 70 mg (as sodium alendronate trihydrate) | 91.4 mg |
| B. | Simethicone granule | 259.0 mg |
| C. | Purified Talc B.P. | 18.0 mg |
| D. | Stearic Acid B.P. | 6.0 mg |
| | Total | 374.4 mg |

The required amount of simeticone granules (in this particular case 259.0 mg) are then mixed with ingredients A, C and D until a uniform mixture is obtained. The mixture is then compressed to a suitable hardness to give tablets.

Example 27

Tablets are prepared as for the method of Example 26 except that the amounts of items B-D are doubled to give a tablet containing 100 mg simeticone with a tablet compression weight of 633.36 mg.

Example 28

Tablets are prepared as for the method of Example 26 except initially using half amounts of ingredients C & D before dry granulation. The compacted granule is then milled and the remainder of items C & D added. The final mix is then blended and compressed to a suitable hardness to give tablets.

Example 29

| | | |
|---|---|---|
| 1. | Etidronate sodium | 200.0 mg |
| 2. | Simeticone B.P. | 50.0 mg |
| 3. | Maize starch B.P. | 20.0 mg |
| 4. | Microcrystalline cellulose | 100.0 mg |
| 5. | Purified water | q.s |
| 6. | Maize starch | 30.0 mg |
| 7. | Colloidal anhydrous silica | 1.5 mg |
| 8. | Magnesium stearate | 7.0 mg |
| | Total | 408.5 mg |

Items 1 & 4 are dry mixed and then item 2 is slowly added until dispersed. A small quantity of water is then added followed by the etidronate disodium. The ingredients are mixed until well dispersed and additional water is added to form a wet granule suitable for compression. The wet granule is then dried and milled and the remaining items are added. The mixture is then compressed at a suitable hardness or encapsulate into a size 1 capsule.

Example 30

Tablets are prepared as for example 26 but alendronate is separately replaced with (a) 35 mg of risedronic acid, (b) 400 mg of sodium clodronate, and (c) 200 mg of tiludronic acid.

Examples 31-41

| Ingredient (mg) | 31 | 32 | 33 | 34 |
|---|---|---|---|---|
| Biphosphonate+ | Q.S | Q.S | Q.S | Q.S |
| Simethicone USP | — | 55.0 | 110.0 | 55.0 |
| Dimethicone NF | 50.0 | — | — | — |
| Mannitol | 300.0 | 270.0 | 320.0 | 300.0 |
| Polyvidone | 3.5 | 3.5 | 14.0 | — |
| Maize Starch | 8.0 | — | — | — |
| Pregelatinised Starch | — | 25.0 | 70.0 | 40.0 |
| Microcrystalline cellulose | 130.0 | 115.0 | 120.0 | 80.0 |
| L-HPC | 20.0 | 32.0 | 30.0 | 30.0 |
| Sodium croscarmellose | 5.0 | 8.0 | 18.0 | — |
| Silicon dioxide | 5.0 | — | — | — |
| Sodium stearyl fumarate | — | — | — | 5.0 |
| Total | 521.5 mg | 508.5 mg | 682.0 mg | 510.0 mg |

| Ingredient (mg) | 35 | 36 | 37 | 38 |
|---|---|---|---|---|
| Biphosphonate+ | q.s | q.s | q.s | q.s |
| Simethicone USP | — | — | 55.0 | 55.0 |
| Dimethicone NF | 50.0 | 100.0 | — | — |
| Lactose hydrous | 300.0 | 360.0 | 300.0 | — |
| Lactose anhydrous | — | — | — | — |
| Mannitol | — | — | — | 250.0 |
| Polyvidone | 3.5 | — | 20.0 | — |
| Gelatin. | — | 18.0 | — | — |
| Maize Starch | 8.0 | 60.0 | — | 7.0 |
| Pregelatinised Starch | — | — | — | — |
| Microcrystalline cellulose | 120.0 | 100.0 | 100.0 | 125.0 |
| L-HPC | 20.0 | 20.0 | 30.0 | 30.0 |
| Sodium croscarmellose Ph.Eur | — | 10.0 | 18.0 | 15.0 |
| Crospovidone | 10.0 | — | — | — |
| Silicon dioxide | 5.0 | 10.0 | — | — |
| Sodium stearyl fumarate | — | 5.0 | — | 5.0 |
| Total | 516.5 mg | 683.0 mg | 523.0 mg | 487.0 mg |

+The therapeutic dose of the biphosphonate.

| | Capsules | | |
|---|---|---|---|
| Ingredient (mg) | 39 | 40 | 41 |
| Biphosphonate+ | q.s | q.s | q.s |
| Simethicone* USP | 110.0 | 55.0 | 110.0 |
| Lactose hydrous | — | — | 180.0 |
| Lactose anhydrous | — | — | — |
| Mannitol | 200.0 | 150.0 | — |
| Gelatin. | — | — | 15.0 |
| Maize Starch | 20.0 | — | — |
| Pregelatinised Starch | — | 20.0 | — |
| Microcrystalline cellulose | 30.0 | 65.0 | 30.0 |
| L-HPC | 10.0 | 10.0 | — |
| Sodium croscarmellose Ph.Eur | 5.0 | 5.0 | 15.0 |
| Crospovidone | — | — | 10.0 |
| Total | 375.0 mg | 305 mg | 360.0 mg |

The invention thus provides formulations and uses thereof for treatment of osteoporosis with reduced gastric and other irritation.

Although the invention has been described with reference to specific examples one of skill in the art will appreciate that variations may be made to these formulations without departing from the scope of the following claims.

The invention claimed is:

1. A formulation consisting essentially of a bisphosphonate in combination with an antifoaming agent in an amount of from 3% to 40% by weight of the formulation, a pharmaceutically acceptable carrier, and one or more of an antacid, a vitamin D derivative, or a calcium supplement, wherein the antifoaming agent is one or more polydimethylsiloxanes, and wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycolate, talc, maize starch, mannitol, pregelatinized starch, low-substituted hydroxypropyl cellulose, silicon dioxide, sodium stearyl fumarate, gelatin, and crospovidone.

2. The formulation of claim 1, wherein the antifoaming agent is present in an amount of from 20 mg to 150 mg.

3. The formulation of claim 2, wherein the antifoaming agent is present in an amount of from 35 mg to 125 mg.

4. The formulation of claim 1, wherein the antifoaming agent is present in an amount of from 5% to 30% by weight of the formulation.

5. The formulation of claim 2, wherein the polydimethylsiloxane is dimethicone BP.

6. The formulation of claim 1, wherein the polydimethylsiloxane is dimethicone BP.

7. The formulation of claim 2, wherein the polydimethylsiloxane is simethicone BP.

8. The formulation of claim 1, wherein the polydimethylsiloxane is simethicone BP.

9. The formulation of claim 2, wherein the polydimethylsiloxane comprises dimethicone BP and simethicone BP.

10. The formulation of claim 1, wherein the polydimethylsiloxane comprises dimethicone BP and simethicone BP.

11. The formulation of claim 1, wherein the formulation contains an antacid.

12. The formulation of claim 11, wherein the antacid is selected from the group consisting of a carbonate salt, a trisilicate, and an oxide salt.

13. The formulation of claim 1, wherein the bisphosphonate is selected from the group consisting of alendronic acid, disodium etidronate, disodium pamidronate, ibandronic acid, risedronate sodium, sodium clodronate, strontium ranelate, tiludronic acid and zoledronic acid.

14. The formulation of claim 1, wherein the bisphosphonate is selected from the group consisting of alendronic acid, alendronate, risedronate and etidronate.

15. The formulation of claim 14, wherein the bisphosphonate is selected from the group consisting of alendronic acid and alendronate.

16. The formulation of claim 1 containing (i) a vitamin D derivative, (ii) a calcium supplement, or (iii) both (i) and (ii).

17. The formulation of claim 16, wherein the vitamin D derivative is selected from the group consisting of ergocalciferol (calciferol, vitamin D2), cholecalciferol (vitamin D3), dihydrotachysterol, alfacalcidol (1α-hydroxycholecalciferol), and calcitriol (1,25-dihydroxycholecalciferol).

18. The formulation of claim 16, wherein the calcium supplement is selected from the group consisting of calcium salts, calcium gluconate, calcium chloride, calcium lactate, calcium carbonate, calcium glubionate and calcium lactobionate, and calcium lactate gluconate and calcium carbonate.

19. A kit consisting essentially of a bisphosphonate in combination with an antifoaming agent in an amount of from 3% to 40% by weight of the formulation, a pharmaceutically acceptable carrier, and one or more of an antacid, a vitamin D derivative, or a calcium supplement, wherein the antifoaming agent is one or more polydimethylsiloxanes, and wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycollate, talc, maize starch, mannitol, pregelatinized starch, low-substituted hydroxypropyl cellulose, silicon dioxide, sodium stearyl fumarate, gelatin, and crospovidone.

20. The kit of claim 19, wherein the antifoaming agent is present in an amount of from 20 mg to 150 mg.

21. The kit of claim 19, wherein the antifoaming agent is present in an amount of from 3% to 20% by weight of the formulation.

22. The kit of claim 19 containing a vitamin D derivative.

23. The kit of claim 19 containing one or more calcium supplements.

24. A method for the treatment of osteoporosis, comprising administering to a patient in need of said treatment a composition consisting essentially of a bisphosphonate in combination with an antifoaming agent in an amount of from 3% to 40% by weight of the formulation, a pharmaceutically acceptable carrier, and one or more of an antacid, a vitamin D derivative, or a calcium supplement, wherein the antifoaming agent is one or more polydimethylsiloxanes, and wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycollate, talc, maize starch, mannitol, pregelatinized starch, low-substituted hydroxypropyl cellulose, silicon dioxide, sodium stearyl fumarate, gelatin, and crospovidone.

25. The method of claim 24, wherein the antifoaming agent is present in an amount of from 20 mg to 150 mg.

26. The method of claim 24, wherein the antifoaming agent is present in an amount of from 3% to 20% by weight of the formulation.

27. A formulation consisting essentially of alendronic acid in an amount of from 10 mg to 70 mg, simethicone in an amount of from wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycollate, talc, maize starch, mannitol, pregelatinized starch, low-substituted hydroxypropyl cellulose, silicon dioxide, sodium stearyl fumarate, gelatin, and crospovidone 7% to 18% by weight of the formulation, and a pharmaceutically acceptable carrier.

28. A formulation consisting essentially of alendronic acid in an amount of from 10 mg,to 70 mg,dimethicone in an amount of from wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycollate, talc, maize starch, mannitol, pregelatinized starch, low-substituted hydroxypropyl cellulose, silicon dioxide, sodium stearyl fumarate, gelatin, and crospovidone 7% to 18% by weight of the formulation, and a pharmaceutically acceptable carrier.

29. A formulation consisting essentially of:
   (a) a bisphosphonate;
   (b) an antifoaming agent in an amount of at least 2% by weight of the formulation, wherein the antifoaming agent is one or more polydimethylsiloxanes;
   (c) one or more of an antacid, a vitamin D derivative, or a calcium supplement; and
   (d) a pharmaceutically acceptable carrier, wherein the pharmaceutically acceptable carrier is selected from the group consisting of one or more of microcrystalline cellulose, lactose, croscarmellose sodium, colloidal anhydrous silica, magnesium stearate, calcium carbonate, povidone, sucrose, stearic acid, sodium starch glycollate, talc, maize starch, mannitol, pregelatinized starch, low-substituted hydroxypropyl cellulose, silicon dioxide, sodium stearyl fumarate, gelatin, and crospovidone.

30. The formulation of 29, wherein the bisphosphonate is selected from the group consisting of alendronic acid, disodium etidronate, disodium pamidronate, ibandronic acid, risedronate sodium, sodium clodronate, strontium ranelate, tiludronic acid and zoledronic acid.

31. The formulation of claim 29, wherein the antifoaming agent is one or more polydimethylsiloxanes.

32. The formulation of 31, wherein the one or more polydimethylsiloxanes is dimethicone BP, simethicone BP, or a combination thereof.

33. The formulation of claim 29, wherein the antifoaming agent is present in an amount of from 20 mg to 150 mg.

34. The formulation of claim 33, wherein the antifoaming agent is present in an amount of from 35 mg to 125 mg.

35. The formulation of claim 29, wherein the antifoaming agent is present in an amount of from 3% to 40% by weight of the formulation.

36. The formulation of claim 35, wherein the antifoaming agent is present in an amount of from 5% to 30% by weight of the formulation.

37. The formulation of claim 29, wherein the antacid is selected from the group consisting of a carbonate salt, a trisilicate, and an oxide salt.

38. The formulation of claim 29, wherein the vitamin D derivative is selected from the group consisting of ergocalciferol (calciferol, vitamin D 2), cholecalciferol (vitamin D 3),dihydrotachysterol, alfacalcidol (1 α-hydroxycholecalciferol), and calcitriol (1,25-dihydroxycholecalciferol).

39. The formulation of claim 29, wherein the calcium supplement is selected from the group consisting of calcium salts, calcium gluconate, calcium chloride, calcium lactate, calcium carbonate, calcium glubionate and calcium lactobionate, and calcium lactate gluconate and calcium carbonate.

* * * * *

UNITED STATES PATENT AND TRADEMARK OFFICE
CERTIFICATE OF CORRECTION

| | | |
|---|---|---|
| PATENT NO. | : 7,473,684 B2 | |
| APPLICATION NO. | : 11/439427 | |
| DATED | : January 6, 2009 | |
| INVENTOR(S) | : Harrison et al. | |

It is certified that error appears in the above-identified patent and that said Letters Patent is hereby corrected as shown below:

In claim 27, column 14, lines 1-3, please delete "A formulation consisting essentially of alendronic acid in an amount of from 10 mg to 70 mg, simethicone in an amount of from" and insert therein -- A formulation consisting essentially of alendronic acid in an amount of from 10 mg to 70 mg, simethicone in an amount of from 7% to 18% by weight of the formulation, and a pharmaceutically acceptable carrier, --.

In claim 27, column 14, lines 10-12, please delete "7% to 18% by weight of the formulation, and a pharmaceutically acceptable carrier".

In claim 28, column 14, lines 13-15, please delete "A formulation consisting essentially of alendronic acid in an amount of from 10 mg,to 70 mg,dimethicone in an amount of from" and insert therein -- A formulation consisting essentially of alendronic acid in an amount of from 10 mg to 70 mg, dimethicone in an amount of from 7% to 18% by weight of the formulation, and a pharmaceutically acceptable carrier, --.

In claim 28, column 14, lines 22-24, please delete "7% to 18% by weight of the formulation, and a pharmaceutically acceptable carrier".

Signed and Sealed this

Twenty-first Day of April, 2009

JOHN DOLL
*Acting Director of the United States Patent and Trademark Office*